United States Patent [19]

Berger

[11] 4,412,078
[45] Oct. 25, 1983

[54] HYDANTOINYLSILANES

[75] Inventor: Abe Berger, Summit, N.J.

[73] Assignee: M & T Chemicals Inc., Woodbridge, N.J.

[21] Appl. No.: 326,318

[22] Filed: Dec. 1, 1981

Related U.S. Application Data

[63] Continuation of Ser. No. 97,902, Nov. 28, 1979, abandoned.

[51] Int. Cl.$^3$ ............................. C07F 7/18; C07F 7/10
[52] U.S. Cl. .................................................... 548/110
[58] Field of Search ............ 548/110, 312 (U.S. only)

[56] References Cited

U.S. PATENT DOCUMENTS 3,692,798  9/1972  Barcza ................................ 548/110
3,892,748  7/1975  Hayao et al. .................... 548/312 X

FOREIGN PATENT DOCUMENTS 49-160273  6/1974  Japan .................................. 548/110
346306  10/1972  U.S.S.R. ............................. 548/110

*Primary Examiner*—Diana G. Rivers
*Attorney, Agent, or Firm*—S. A. Marcus; F. Schoenberg; S. H. Parker

[57] ABSTRACT

This invention relates to a novel class of organosilanes. The characteristic feature of these silanes is the presence of a hydantoin residue that is bonded to silicon through an alkylene group.

12 Claims, No Drawings

HYDANTOINYLSILANES

This is a continuation, of application Ser. No. 097,902 filed Nov. 28, 1979, now abandoned.

BACKGROUND OF THE INVENTION

This invention relates to a novel class of organosilanes. The characteristic feature of these silanes is the presence of a hydantoin residue that is bonded to silicon through an alkylene group.

SUMMARY OF THE INVENTION

The organosilanes of this invention exhibit the general formulae

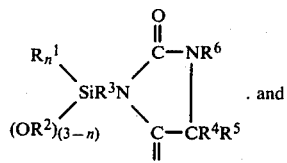
. and

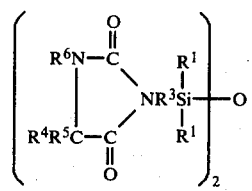

wherein $R^1$ is selected from the group consisting of alkyl, aryl, cyanoalkyl, trifluoropropyl, alkenyl, alkynyl and halophenyl; $R^2$ is selected from the group consisting of alkyl, alkaryl and cycloalkyl; $R^3$ is alkylene; $R^4$ and $R^5$ are individually selected from the group consisting of hydrogen, alkyl, aryl, aralkyl and alkaryl; $R^6$ is

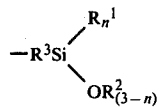

or is selected from the same group as $R^4$ and n is 0, 1, 2 or 3 with the proviso that any alkyl or alkylene group contains from 1 to 12 carbon atoms and any alkenyl or alkynyl group contains from 2 to 12 carbon atoms.

This invention also provides a method for preparing a hydantoinyl silane, said method consisting essentially of the following steps:

(1) Reacting substantially equimolar amounts of (a) an anhydrous alkali metal salt of a hydantoin represented by the general formula

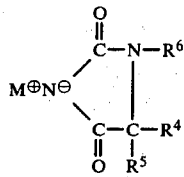

wherein M represents an alkali metal and (b) a haloalkylsilane represented by the general formula

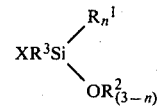

in a reaction medium comprising a dipolar, aprotic liquid;

(2) maintaining the mixture containing the hydantoin salt and said haloalkylsilane at a temperature of from ambient to the boiling point of said mixture for a period of time sufficient to obtain a substantially complete reaction, and (3) isolating said hydantoinyl silane from the reaction mixture.

DETAILED DESCRIPTION OF THE INVENTION

The novel silanes of this invention can be prepared using conventional procedures employed for reacting halosilanes with compounds containing a labile proton. A preferred method involves the reaction of an anhydrous alkali metal salt of hydanotoin or one of the substituted hydantoins represented by the formula

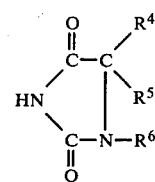

with a haloalkylsilane represented by the formula

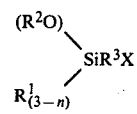

wherein X represents chlorine, bromine or iodine. This reaction is preferably conducted in the presence of a dipolar aprotic organic liquid medium which is a solvent for the aforementioned alkali metal salt of the hydantoin. Suitable dipolar aprotic liquids include N,N-dimethylformamide, N-methylpyrrolidone and dimethylsulfoxide.

Since the reaction between the hydantoin salt and the haloalkyl silane may be exothermic, it is preferable to first dissolve the hydantoin salt in the liquid reaction medium and gradually add the haloalkylsilane to the resultant solution under an inert atmosphere such as nitrogen to exclude even trace amounts of water, which would rapidly hydrolyze the alkoxy groups present on the haloalkylsilane. It is often desirable to heat the reaction mixture at temperatures of from 40° to about 100° C. for from 0.5 to 5 hours or longer to ensure that the reaction is complete. The reaction product is often soluble in the reaction medium, in which instance the product is readily isolated by filtering to remove the solid alkali metal halide byproduct and distilling the dipolar aprotic liquid under reduced pressure to minimize heat-induced decomposition of the desired product.

The product of the aforementioned reaction contains one silicon atom and one hydantoin residue that is bonded to silicon through an alkylene group represented by $R^3$ in the foregoing formula. Compounds containing 3 hydrocarbyl and 1 hydrocarbyloxy group bonded to silicon are readily converted to the corresponding bis(hydantoinylalkyl)tetrahydrocarbyldisiloxane by hydrolysis in the presence of a methanol-water or ethanol-water mixture containing a trace amount of an alkali metal hydroxide such as potassium hydroxide.

The hydantion employed to prepared the compounds of this invention can be unsubstituted, in which instance the substituents represented by $R^4$, $R^5$ and $R^6$ in the foregoing formulae are hydrogen. Alternatively, one can employ any of the available substituted hydantoins or a compound containing the desired substituents can be prepared using synthetic procedures and reactions disclosed in the chemical literature. Representative substituted hydantoins which are commercially available or have been reported in the chemical literature include 5,5-dimethylhydantoin
5,5-diphenylhydantoin
5-ethyl-5-(2-methylbutyl)hydantoin
5-phenylhydantoin The synthesis of hydantoin, also referred to as 2,4-diketoiminazolidine, and a number of substituted hydantoins, is described in a text entitled "Chemistry of Carbon Compounds" edited by E. H. Rodd (Elsiner Publishing Company, 1957) and in an article by E. Ware [Chemical Reviews 46, 403–470 (1950)].

The following examples describe the preparation of 4 preferred species selected from the present class of novel silanes and disiloxanes. These examples should not be considered as limiting the scope of the accompanying claims.

EXAMPLE 1—Preparation of 5,5-dimethyl-3-trimethoxysilylpropyl Hydantoin

A mixture containing 12.8 g (0.1 mole) 5,5-dimethylhydantoin, 5.6 g (0.1 mole) potassium hydroxide and 100 cc ethanol was heated to the boiling point until a clear solution was obtained. The ethanol was then evaporated under reduced pressure to isolate the solid, anhydrous salt. The salt was combined with 100 cc of dry N,N-dimethylformamide and the resultant mixture was heated at 50° C. until a clear solution formed. A 19.8 g (0.1 mole) portion of chloropropyl trimethoxysilane was then added dropwise to the aforementioned salt solution under a nitrogen atmosphere with stirring. The temperature of the reaction mixture increased slightly during the addition, which is indicative of an exothermic reaction, and a white precipitate (potassium chloride) began to form when the silane addition was begun. Following completion of the addition the reaction mixture was heated at 95° C. for three hours. Analysis by vapor phase chromatography of the liquid phase demonstrated that the initial chloropropyl trimethoxysilane had been converted to a product exhibiting a high retention time. The reaction mixture was then cooled and filtered, following which the liquid phase was distilled to remove the N,N-dimethylformamide. A second fraction was collected at a temperature of 194° C. and a pressure of 4 mm of mercury and subsequently solidified to a white solid. Analysis by vapor phase chromatography indicated that this material was 98% pure and contained a trace amount of the initial hydantoin. The infra-red spectrum of the material was consistent with the proposed structure

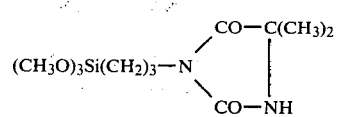

The product was found to contain 9.74% by weight of silicon and 9.92% nitrogen. The calculated values for the expected product are 9.64% silicon and 9.66% nitrogen.

EXAMPLE 2—Preparation of 3-Dimethoxymethylsilylpropylhydantoin

A mixture containing 10.0 g (0.1 mole) hydantoin, 5.6 g (0.1 mole) potassium hydroxide and 100 cc ethanol was heated to the boiling point until a clear solution was obtained. The resultant salt was then isolated and dried as described in the preceeding example, following which it was solubilized in 100 cc of anhydrous N,N-dimethylformamide and reacted with 18.2 g of chloropropylmethyldimethoxysilane under a nitrogen atmosphere using dropwise addition. The reaction mixture was heated at 110° C. for about sixteen hours following completion of the silane addition. The reaction mixture was then cooled and filtered to remove the potassium chloride byproduct. Analysis of the liquid phase by vapor phase chromatography demonstrated that the original silane had been consumed and replaced by a material having a significantly longer retention time. The desired product was recovered following distillation to remove the N,N-dimethylformamide.

EXAMPLE 3—Preparation of Bis[5,5-dimethylhydantoin-3-yl)propyl]tetramethyldisiloxane A sample of 5,5-dimethyl-3-dimethylmethoxysilylpropylhydantoin was prepared and isolated using the general procedure described in the preceeding examples with 0.1 mole of each of the three reagents, namely 5,5-dimethylhydantoin, 3-chloropropyldimethylmethoxysilane and potassium hydroxide. A 24.4 g portion of the final product was dissolved in a mixture of 5.4 g of water and 300 cc methanol containing one pellet of potassium hydroxide. The resultant mixture was stirred at ambient temperature for 16 hours, at which time the methanol-water mixture was removed by distillation under reduced pressure. The identity of the final product as a disiloxane was confirmed by its infra-red spectrum and by vapor phase chromatography.

EXAMPLE 4—Preparation of 1,3-Bis(trimethoxysilylpropyl)-5,5-dimethylhydantoin A 2.4 g portion of a dispersion containing 50% by weight of sodium hydride in a liquid paraffin was added in portions under an inert atmosphere to a solution containing 14.5 g (0.05 mole) 5,5-dimethyl-3-trimethoxysilylpropyl hydantoin and 150 cc of anhydrous N,N-dimethylformamide. The temperature of the reaction mixture was maintained at from 15° to 20° C. during the addition of the hydride. Following completion of the addition the mixture was stirred until hydrogen evolution ceased, at which time it was heated to 85° C., and 98.8 g of chloropropyltrimethoxysilane were added dropwise to the reaction mixture. A white precipitate formed as the addition progressed. Following completion of the addition the reaction mixture was heated at 95° C. for 16 hours, at which time the reaction mixture was cooled, filtered and the liquid phase distilled under reduced pressure to remove the N,N-dimethylformamide. The liquid paraffin was washed from the product using hexane. The identity of the residue as the expected silylhydantoin was confirmed using infra-red and nuclear magnetic resonance spectroscopy.

The silanes and disiloxanes of this invention are particularly useful as coupling agents for bonding glass fibers to organic resins and as self-bonding adhesion promoters for room temperature curable silicone adhesives. Some prior art room temperature curable polysiloxane products employing an acetoxysilane as the curing agent require a primer to achieve adequate adhesion with the substrate to which they are applied. Primers are not required using the hydantoinyl silanes of this invention.

What is claimed is:

1. A hydantoinyl silane represented by the generic formula

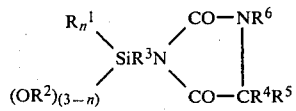

wherein $R^1$ is selected from the group consisting of alkyl, aryl, cyanoalkyl, trifluoropropyl, alkenyl, alkynyl and halophenyl; $R^2$ is selected from the group consisting of alkyl, alkaryl and cycloalkyl; $R^3$ is alkylene; $R^4$ and $R^5$ are individually selected from the group consisting of hydrogen, alkyl, phenyl and alkaryl; $R^6$ is

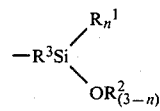

or is selected from the same group as $R^4$ and n is 0, 1, 2 or 3 with the proviso that any alkyl or alkylene group contains from 1 to 12 carbon atoms and any alkenyl or alkynyl group contains from 2 to 12 carbon atoms.

2. A silane according to claim 1 wherein $R^1$ and $R^2$ are alkyl.

3. A silane according to claim 2 wherein $R^1$ and $R^2$ are methyl.

4. A silane according to claim 1 wherein $R^4$ and $R^5$ are hydrogen or alkyl.

5. A silane according to claim 4 wherein $R^4$ and $R^5$ are methyl.

6. A silane according to claim 1 wherein $R^6$ is hydrogen or

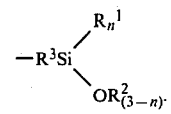

7. A silane according to claim 1 wherein $R^3$ is propyl.

8. A bis(hydantoinyl)disiloxane represented by the general formula

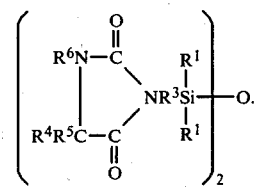

wherein $R^1$ is selected from the group consisting of alkyl, aryl, cyanoalkyl, trifluoropropyl, alkenyl, alkynyl and halophenyl; $R^3$ is alkylene; $R^4$ and $R^5$ are individually selected from the group consisting of hydrogen, alkyl, phenyl and aralkyl; and $R^6$ is

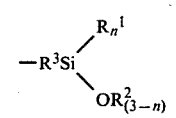

or is selected from the same group as $R^4$, with the proviso that any alkyl or alkylene group contains from 1 to 12 carbon atoms and any alkenyl or alkynyl group contains from 2 to 12 carbon atoms.

9. A disiloxane according to claim 8 wherein $R^1$ is alkyl.

10. A disiloxane according to claim 9 wherein $R^1$ is methyl.

11. A disiloxane according to claim 8 wherein $R^4$ and $R^5$ are hydrogen or alkyl.

12. A disiloxane according to claim 11 wherein $R^4$ and $R^5$ are methyl.

* * * * *